United States Patent [19]
Ando et al.

[11] Patent Number: 5,608,156
[45] Date of Patent: Mar. 4, 1997

[54] METHOD FOR DETECTING THE CONCENTRATION OF THE HYDROGEN PEROXIDE VAPOR AND THE APPARATUS THEREFOR

[75] Inventors: Shinichi Ando, Tokorozawa; Taizo Ichida, Ibaragi-ken, both of Japan

[73] Assignee: Taiyo Toyo Sanso Co., Ltd., Osaka, Japan

[21] Appl. No.: 481,039

[22] Filed: Jun. 23, 1995

[30] Foreign Application Priority Data

May 24, 1995 [JP] Japan .................................. 7-124715

[51] Int. Cl.$^6$ .................. G01N 27/12; G01N 33/02; G01D 18/00
[52] U.S. Cl. .................. 73/31.06; 73/23.28; 73/29.01; 73/335.05; 422/83; 422/90
[58] Field of Search .................. 73/23.28, 23.21, 73/29.01, 31.06, 335.05; 422/83, 88, 90, 98

[56] References Cited

U.S. PATENT DOCUMENTS

| | | | |
|---|---|---|---|
| 3,031,882 | 5/1962 | Thayer et al. | 73/27 |
| 4,050,995 | 9/1977 | Bredeweg | 204/1 T |
| 4,141,237 | 2/1979 | Deford et al. | 73/23.1 |
| 4,535,315 | 8/1985 | Sakai | 338/34 |
| 4,569,826 | 2/1986 | Shiratori et al. | 422/90 |
| 4,792,433 | 12/1988 | Katsura et al. | 422/98 |
| 4,992,965 | 2/1991 | Hölter et al. | 364/551.01 |
| 5,033,284 | 7/1991 | Belt et al. | 73/1 G |
| 5,041,186 | 8/1991 | Nishio et al. | 156/620.2 |
| 5,088,314 | 2/1992 | Takashi | 73/23.21 |
| 5,106,756 | 4/1992 | Zaromb | 436/161 |
| 5,264,833 | 11/1993 | Jeffers et al. | 340/632 |
| 5,270,009 | 12/1993 | Nakamori et al. | 422/83 |

*Primary Examiner*—Hezron E. Williams
*Assistant Examiner*—J. David Wiggins
*Attorney, Agent, or Firm*—Griffin, Butler, Whisenhunt & Kurtossy

[57] ABSTRACT

The disclosure where the hydrogen peroxide vapor 4a is supplied to a treatment vessel, and a subject 1 to be treated in the treatment vessel 2 is subjected to a sterilization treatment by contact with the hydrogen peroxide vapor 4a, the concentration of the hydrogen peroxide vapor 4a in the treatment vessel 2 is detected directly and accurately on a real-time basis by a semiconductor gas sensor 8.

6 Claims, 4 Drawing Sheets

METHOD FOR DETECTING THE CONCENTRATION OF THE HYDROGEN PEROXIDE VAPOR AND THE APPARATUS THEREFOR

BACKGROUND OF THE INVENTION

The present invention relates to a method for detecting the concentration of the hydrogen peroxide vapor in a treatment vessel and an apparatus for practicing the method where hydrogen peroxide vapor is supplied to a treatment vessel to conduct a treatment, such as a sterilization treatment, by means of contact of the subject to be treated in the treatment vessel with hydrogen peroxide vapor.

Since hydrogen peroxide vapor is naturally decomposed into harmless oxygen and water by contact with a solid and generates nascent oxygen having a sterilizing effect and the like, it is a safe and simple agent for various treatments such as a sterilization and the like, and a wide range of utilization thereof is expected. In the field of manufacturing of medicines and medical instruments, and in the field of foods processing, packaging materials for the ground materials of medicines and foods have been heretofore subjected to the sterilization treatment by the hydrogen peroxide vapor. That is, the sterilization treatment of the subject to be treated is performed by contact with the hydrogen peroxide vapor, which is supplied into a treatment vessel which has housed therein the subject to be treated such as a packaging material and the like, under conditions such that the pressure within the vessel is higher than atmospheric pressure and the concentration of the hydrogen peroxide vapor in the treatment vessel is higher than a predetermined level.

Since the hydrogen peroxide vapor supplied into the treatment vessel is easily decomposed and consumed due to contact with the subject to be treated or the wall face inside the vessel, the concentration thereof decreases with the lapse of time. On the other hand, because the sterilization treatment by hydrogen peroxide vapor is performed by means of nascent oxygen generated by the decomposition of hydrogen peroxide, therefore, when the concentration of the hydrogen peroxide vapor decreases to a level less than a certain value, the effective sterilization treatment function cannot be effected. However, it is wasteful from the standpoint of the sterilization treatment to oversupply the hydrogen peroxide vapor into the treatment vessel to maintain the concentration of the vapor higher than a required level. Also, he economic burden is large because, for instance, a treatment device for making the hydrogen peroxide vapor harmless, used when emitting the excess hydrogen peroxide vapor into the air, becomes large sized.

Therefore, in order to perform the sterilization treatment efficiently, it is required to maintain and control the concentration of the hydrogen peroxide vapor in the treatment vessel in a proper concentration range to effect an effective sterilization treatment. In order to control the concentration properly, it is required to detect the concentration of the hydrogen peroxide vapor in the treatment vessel directly and accurately on a real-time basis.

Conventionally, however, a method to detect the concentration of hydrogen peroxide vapor directly and on a real-time basis has not been proposed at all, and the sterilization treatment has thus not been efficiently performed.

Therefore, the inventors of the present invention have tried to detect directly the concentration of the hydrogen peroxide vapor by a controlled potential electrolysis method, test-paper photoelectric photometry, and a method using a detection tube.

Namely, the controlled potential electrolysis method uses a concentration detector (HF sensor) comprising a working electrode and an electrode couple arranged in the region for containing the electrolytic solution, which is separated from the outside world by a partition. And when the hydrogen peroxide vapor permeates the partition and diffuses into the region for containing the electrolytic solution, it is adsorbed to the working electrode comprising an electrochemical catalyst, and causes the oxidation or reduction reaction to generate electric current between the electrodes, thereby detecting the concentration of the hydrogen peroxide vapor by the amount of the generated current.

In such a method, however, not only in the case where the hydrogen peroxide vapor to be detected has extremely low concentration (for example, not higher than 10 ppm), but also in the case of the hydrogen peroxide vapor having concentration as high as the level which permits the sterilization treatment to be sufficiently performed (for example, not lower than 500 ppm), the hydrogen peroxide vapor, the gas to be detected, which has diffused into the electrolytic solution-containing region is adsorbed by the electrolytic solution and remains therein after the concentration has been detected (i.e., after the sterilization treatment has been completed and the hydrogen peroxide vapor within the treatment vessel has been completely removed), and the hydrogen peroxide adsorbed to the working electrode is not eliminated for a long period of time. Therefore, the response to the change in the concentration of the hydrogen peroxide vapor is extremely bad, and the concentration of the hydrogen peroxide vapor cannot be detected accurately on a real-time basis (see FIG. 6).

Furthermore, the test-paper photoelectric photometry uses a concentration detector which incorporates a test paper which is subjected to a special treatment by chemicals so that it is colored by contact with the hydrogen peroxide vapor and detects the concentration of the hydrogen peroxide vapor by the degree of the test paper. In addition to the above-mentioned chemicals, an adequate quantity of water is impregnated into the test paper so as to promote the coloration. In such a method, however, since water is impregnated into the test paper, when the hydrogen peroxide vapor contacts with the test paper, the hydrogen peroxide vapor dissolves in the water contained in the test paper, thereby changing the concentration of the hydrogen peroxide vapor in the vicinity of the concentration detector, with the result that accurate detection of the concentration cannot be performed.

In the sterilization treatment by the hydrogen peroxide vapor, when water adheres to the surface of the object to be treated, the hydrogen peroxide vapor dissolves, as described above, and there is a threat that the sterilization of the object to be treated due to contact with the hydrogen peroxide vapor may be weakened. Therefore, drying treatment may be conducted after the object to be treated is housed in the treatment vessel. When such a drying treatment is performed, however, the test paper which is incorporated in the concentration detector disposed in the treatment vessel is also dried, and the water contained in the test paper is vaporized. Therefore, the detection of the concentration of the hydrogen peroxide vapor using the test paper may not be able to be performed accurately. Moreover, the chemicals impregnated into the test paper may be vaporized by the drying treatment to contaminate the object to be treated. Thus, test-paper photoelectric photometry is inappropriate and cannot be adopted as a detection method for detecting the concentration of the hydrogen peroxide vapor in the sterilization treatment, which needs to be conducted in a low humidity atmosphere.

A method using a detection tube uses a concentration detector, in which a detection agent which changes color by a chemical reaction caused by contact with the hydrogen peroxide vapor is filled in a glass tube, and detects the concentration of the hydrogen peroxide vapor by measuring by the scale of the glass tube the length of the portion of the detection agent whose color has changed. In such a method, however, continuous detection of the concentration cannot be performed, and the concentration of the hydrogen peroxide vapor cannot be detected on a real-time basis.

Thus, neither detection method can detect the concentration of the hydrogen peroxide vapor on a real-time basis, and can be adopted for the treatment of the hydrogen peroxide vapor, such as a sterilization treatment.

SUMMARY OF THE INVENTION

The object of the present invention is, therefore, to provide a method to detect the concentration of the hydrogen peroxide vapor which can detect the concentration of the hydrogen peroxide vapor directly and accurately on a real-time basis to perform the treatment of the hydrogen peroxide vapor such as a sterilization treatment and the like efficiently and effectively, and to provide an apparatus for detecting the concentration.

In method for detecting the concentration of the hydrogen peroxide vapor according to the present invention, when the concentration of the hydrogen peroxide vapor supplied to a treatment vessel is to be detected, in order to attain the above object, it is proposed to arrange a semiconductor gas sensor and a concentration indicator, respectively, inside and outside the treatment vessel, and to convert the output of the semiconductor gas sensor to the concentration of the hydrogen peroxide vapor to indicate the concentration by a concentration indicator.

Furthermore, the apparatus for detecting the concentration of hydrogen peroxide vapor according to the present invention to implement this method includes a semiconductor gas sensor arranged in the treatment vessel which can house an object to be treated, and a concentration indicator arranged outside the treatment vessel. The semiconductor gas sensor has a sensor element made of metal oxide which is brought into contact with the hydrogen peroxide vapor supplied into the treatment vessel to change the conductivity, and the concentration indicator converts the output of the semiconductor gas sensor to the concentration of the hydrogen peroxide vapor to indicate the concentration thereof.

The hydrogen peroxide vapor in the treatment vessel is chemically adsorbed to the oxide semiconductor element of the semiconductor gas sensor. As a result, migration of free electrons occurs in the element to increase the conductivity of the element. The reaction speed thereof is quite high (several tens of seconds), and the sensor output quickly responds to the change of the concentration, thereby allowing the concentration of the hydrogen peroxide vapor to be detected directly and accurately on a real-time basis. Therefore, because the concentration of the hydrogen peroxide vapor in the treatment vessel can be properly maintained and controlled, the sterilization treatment and the like by the hydrogen peroxide vapor can be efficiently and effectively performed.

When the hydrogen peroxide vapor is supplied into a treatment vessel maintained in an air atmosphere, the sensor output and the concentration of the hydrogen peroxide vapor are always proportional and regardless of the sensor output, the conversion scale or factor of data output signals from the sensor output to the indicated concentration is fixed, and if the concentration of the hydrogen peroxide vapor is identical, the sensor output shows always the same value. However, this conversion rate is always fixed so long as the implementation conditions (i.e., the conditions for supplying the hydrogen peroxide vapor to the treatment vessel and the conditions for treating the object to be treated by the hydrogen peroxide vapor) are the same. The conversion rate is set in advance according to the implementation conditions. That is, experiments are conducted under the same conditions with the implementation conditions to determine the data of the correlation between the sensor output and the concentration of the hydrogen peroxide vapor, and the conversion rate is set based on this data.

On the other hand, when the hydrogen peroxide vapor is supplied into the treatment vessel maintained in a vacuum (less than 760 Torr), the interrelation between the sensor output and the concentration of the hydrogen peroxide vapor is changed due to the pressure within the treatment vessel and is not constant. Hence, even if the concentration of the hydrogen peroxide vapor is the same, the sensor output may not show the same value. Therefore, in such a case, the data of the interrelation between the sensor output and the concentration of the hydrogen peroxide vapor under the corresponding pressure conditions is obtained in advance, using the pressure as an independent parameter, and based on this data, the concentration of the hydrogen peroxide vapor obtained at the sensor output is arithmetically corrected by a computing unit, and the corrected value is indicated by the concentration indicator.

DESCRIPTION OF THE PREFERRED EMBODIMENTS

Figure 1:
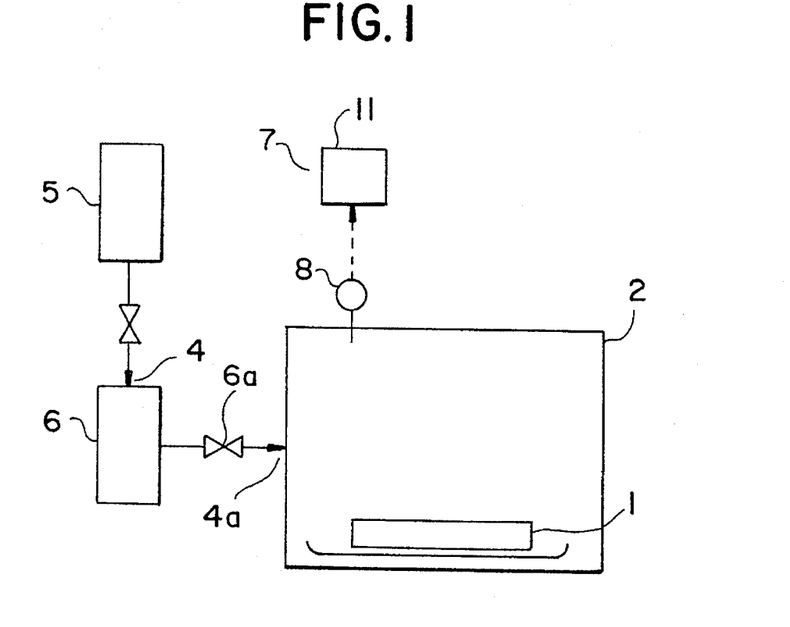
FIG. 1 is a systematic view of the sterilization treatment system showing one embodiment of the concentration detecting apparatus according to the present invention.
Figure 2:
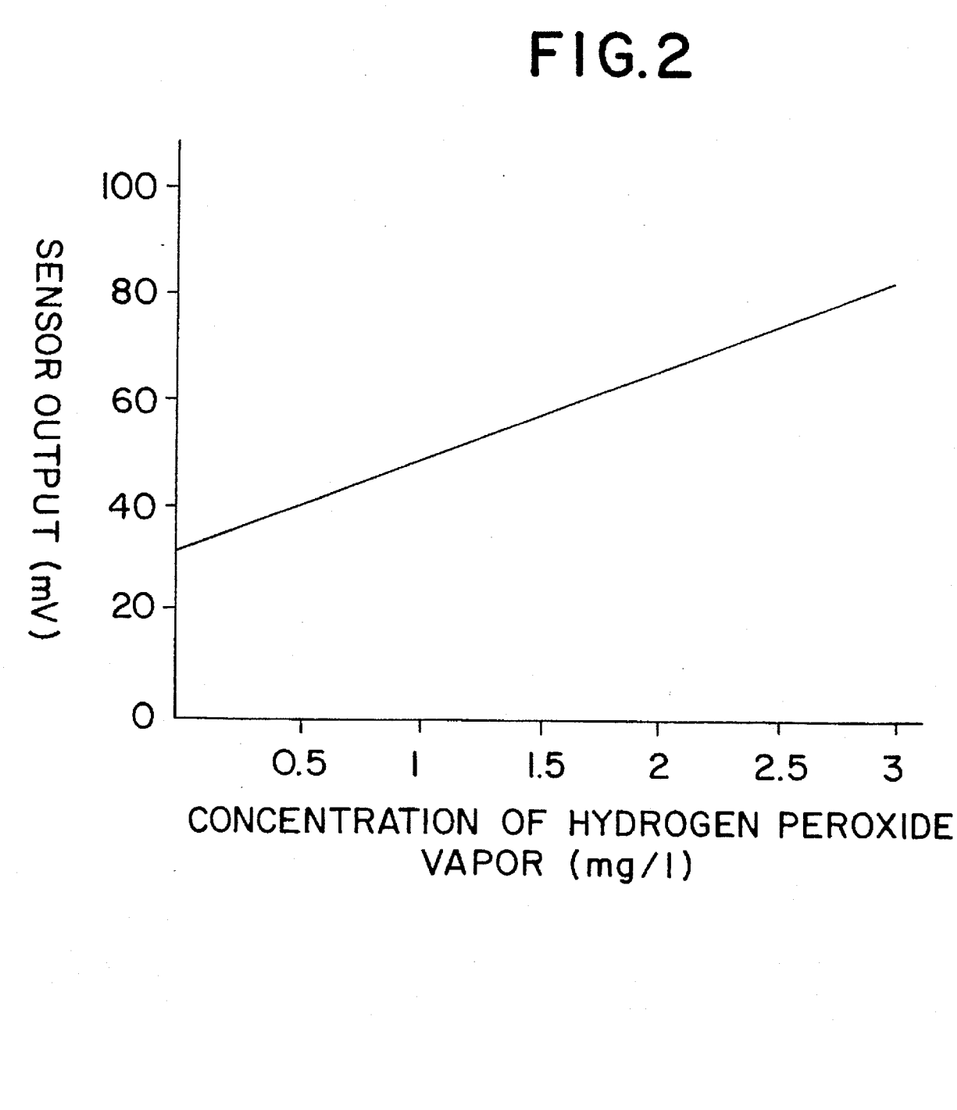
FIG. 2 is a graph showing the interrelation between the output of the semiconductor gas sensor and the concentration of the hydrogen peroxide vapor.

The structure of the present invention will now be described in detail with reference to each embodiment shown in FIGS. 1 and 2.

The embodiment is concerned with an example in which the present invention is applied to the sterilization treatment system of the base materials of medicine or the like. That is, this sterilization treatment system comprises as shown in FIG. 1, a treatment vessel 2 into/out of which an object 1 to be treated can be freely carried, a storage tank 5 of hydrogen peroxide aqueous solution 4, a gasifying device 6 which heats and gasifies the hydrogen peroxide aqueous solution 4 supplied from the storage tank 5 by a heater, and a concentration detection apparatus 7.

The treatment vessel 2 has a sufficient capacity to house the object 1 to be treated, at the time of carrying in/out the subject 1 to be treated, the treatment vessel 2 is maintained in a clean air atmosphere which does not contain the hydrogen peroxide vapor. The storage tank 5 stores hydrogen peroxide aqueous solution (in this embodiment, hydrogen peroxide water having the concentration of 50.14%, and the specific gravity of 1.196), and supplies a predetermined amount thereof to the gasifying device 6, according to need. The gasifying device 6 gasifies the hydrogen peroxide aqueous solution 4 supplied from the storage tank 5, and supplies a predetermined amount of the vapor 4a to the treatment vessel 2 by closing/opening the supply valve 6a. The supply means of the hydrogen peroxide vapor 4a is optional, so long as the hydrogen peroxide vapor 4a can be supplied into the treatment vessel 2 in an air atmosphere. For example, when the pressure of the hydrogen peroxide vapor 4a supplied from the gasifying device 6 to the treatment vessel 2 is low, and the supply thereof to the treatment vessel 2 is not performed well, the hydrogen peroxide vapor 4a is supplied to the treatment vessel 2 with a suitable carrier gas (for example, dried air). The supply of the hydrogen peroxide vapor 4a makes the pressure within the treatment vessel 2 higher than the atmospheric pressure. Namely, the sterilization treatment of the object to be treated is carried out in an atmosphere of the hydrogen peroxide vapor higher than the atmospheric pressure. Furthermore, the temperature in the treatment vessel 2 at the time of sterilization treatment of the subject to be treated becomes generally 5° C. to 80° C.

The concentration detecting apparatus 7 comprises a semiconductor gas sensor 8 arranged inside the treatment vessel 2 and a concentration indicator 11 arranged outside the treatment vessel 2.

The semiconductor gas sensor 8 includes a sensor element made of a metal oxide sintered product whose conductivity changes in contact with the hydrogen peroxide vapor 4a, and a means (indirectly heating type of directly heating type) for heating the electrode embedded in the sensor element and the sensor element. That is, it utilizes the fact that the free electrons in the vicinity of the surface migrate to change the conductivity where such electrons are released by the adsorption of gas components to the surface of oxide particles such as n-type semiconductor oxides (for example, $SnO_2$, $ZnO$, $V_2O_5$, $\gamma-Fe_2O_3$, $TiO_2$ or $CdO$) and p-type semiconductor oxides (for example, $NiO$, $Cr_2O_3$, $Cu_2O$, $MnO_2$ or $MnO$) which constitute the sensor element. The increase of the conductivity due to contact with the hydrogen peroxide vapor 4a, that is, the decrease of the resistance value, is converted to the increase of the voltage in the electric circuit, which has electrical device means for outputting the value. Incidentally, the sensor element is heated so as to increase the rate of adsorption of the gas and oxygen to be detected to trigger desorption from the semiconductor surface and to increase the response rate to detect the gas, but the heating temperature is preferably set generally to 200° C. to 400° C. In this embodiment, a leak detecting sensor on the market (#812, produced by Figaro Giken Co., Ltd.) which detects carbon monoxide is used as the semiconductor gas sensor 8. This #812 produced by Figaro Giken Co., Ltd. has a sensor element made of $SnO_2$ sintered product, and is so constructed as to be heated to 250° C. by a nichrome wire laid inside.

The concentration indicator 11 always receives the output signal from the semiconductor gas sensor 8, and the output from the semiconductor gas sensor 8 is converted to the concentration of the hydrogen peroxide vapor for indication.

Incidentally, this conversion rate is set on the basis of data obtained in advance by experiments, and this data is obtained as described below using the same sensor as the above-mentioned semiconductor gas sensor 8.

Namely, into a test vessel (a heat-resistant glass vessel having the capacity of 2.37 l) in a sealed state, whose inside is in the clean air atmosphere, is injected by microsyringe hydrogen peroxide aqueous solution having the same properties as that stored in said storage tank 5 (hydrogen peroxide water having the concentration of 50.14% and the specific gravity of 1.196). The hydrogen peroxide aqueous solution is instantaneously heated by a heater and the like and gasified completely, and the output (the decrease of the resistance value converted to the increase of the voltage in an electric circuit, as described above) from the semiconductor gas sensor (the same sensor as the above-mentioned semiconductor gas sensor 8 (#812 produced by Figaro Giken Co., Ltd.)) installed in the test vessel was measured at the standard temperature (25° C. to 30° C.). At this time, the injected quantity of the hydrogen peroxide aqueous solution was changed, and the sensor output was measured with respect to each injected quantity. Thus, the interrelation between the data output which was the measured value and the data concentration which was the concentration of the hydrogen peroxide vapor in the test vessel was obtained. The results are as shown in FIG. 2. As is obvious from FIG. 2, the sensor output and the concentration of the hydrogen peroxide vapor have a certain relation, and the conversion rate from the sensor output to the concentration of the hydrogen peroxide vapor can be easily obtained. Therefore, the conversion rate as obtained is fixed. At this conversion rate, the output of the semiconductor gas sensor 8 is converted and indicated as the concentration of the hydrogen peroxide vapor 4a in the treatment vessel 2 by the concentration indicator 11. In addition, the data concentration in the above experiment can be obtained from the capacity of the test vessel, the concentration of hydrogen peroxide aqueous solution and the injection quantity. For example, the data concentration, in the case where the injection quantity is 9 μl, 6 μl, and 3 μl, becomes 2.28 mg —$H_2O_2$/l. 1.52 mg—$H_2O_2$/f. and 0.76 mg —$H_2O_2$/l, respectively.

In the above-mentioned sterilization treatment system, the object 1 to be treated is carried into the treatment vessel 2 which is maintained in a clean air atmosphere, and housed therein. A suitable amount of the hydrogen peroxide vapor 4a is supplied to the treatment vessel 2 to sterilize the object 1 to be treated, while maintaining the concentration of the hydrogen peroxide vapor 4a in the treatment vessel 2 in a predetermined range. Then, after the sterilization treatment of the object 1 to be treated is completed, the object 1 is taken out of the treatment vessel 2. And after the treatment vessel 2 is returned to the state of the clean air atmosphere, a new subject 1 to be treated is carried into the treatment vessel 2 and housed therein. Then the same sterilization treatment is carried out in the manner as mentioned above. Thereafter, by repeating the process of carrying-out of the object as treated, purification of the inside of the treatment vessel, carrying-in of a new object to be treated, housing the same therein, and the sterilization treatment by the hydrogen peroxide vapor 4a in a fixed cycle, the sterilization treatment of the object 1 to be treated can be continuously performed.

At this time, the concentration of the hydrogen peroxide vapor 4a in the treatment vessel 2 can be detected directly and accurately on a real-time basis by the concentration detecting apparatus 7.

Namely, the hydrogen peroxide vapor 4a in the treatment vessel 2 is chemically adsorbed to the oxide semiconductor element of the semiconductor gas sensor 8, depending upon the concentration. As a result, free electrons migrate in the element to increase the conductivity of the element. And the decrease of the resistance value due to the increase of the conductivity is converted to the increase of voltage in the electric circuit, is input to the concentration indicator 11 as a sensor output, and is indicated as the concentration of the hydrogen peroxide vapor at the predetermined conversion rate. Therefore, the concentration of the hydrogen peroxide vapor 4a in the treatment vessel 2 can be accurately detected visually. Furthermore, the conductivity of the element changes with the change of the concentration of the hydrogen peroxide vapor, but such reaction rate is extremely high (several tens of seconds), and the sensor output responds quickly to the change of the concentration. As a result, the concentration of the hydrogen peroxide vapor can be detected accurately on a real-time basis by the indication of the concentration indicator 11. Accordingly, maintenance and control of the concentration of the hydrogen peroxide vapor during the sterilization treatment, and purification control within the treatment vessel 2 at the time of carrying the object 1 to be treated in the vessel 2 and taking out the same can be conducted properly.

Figure 3:
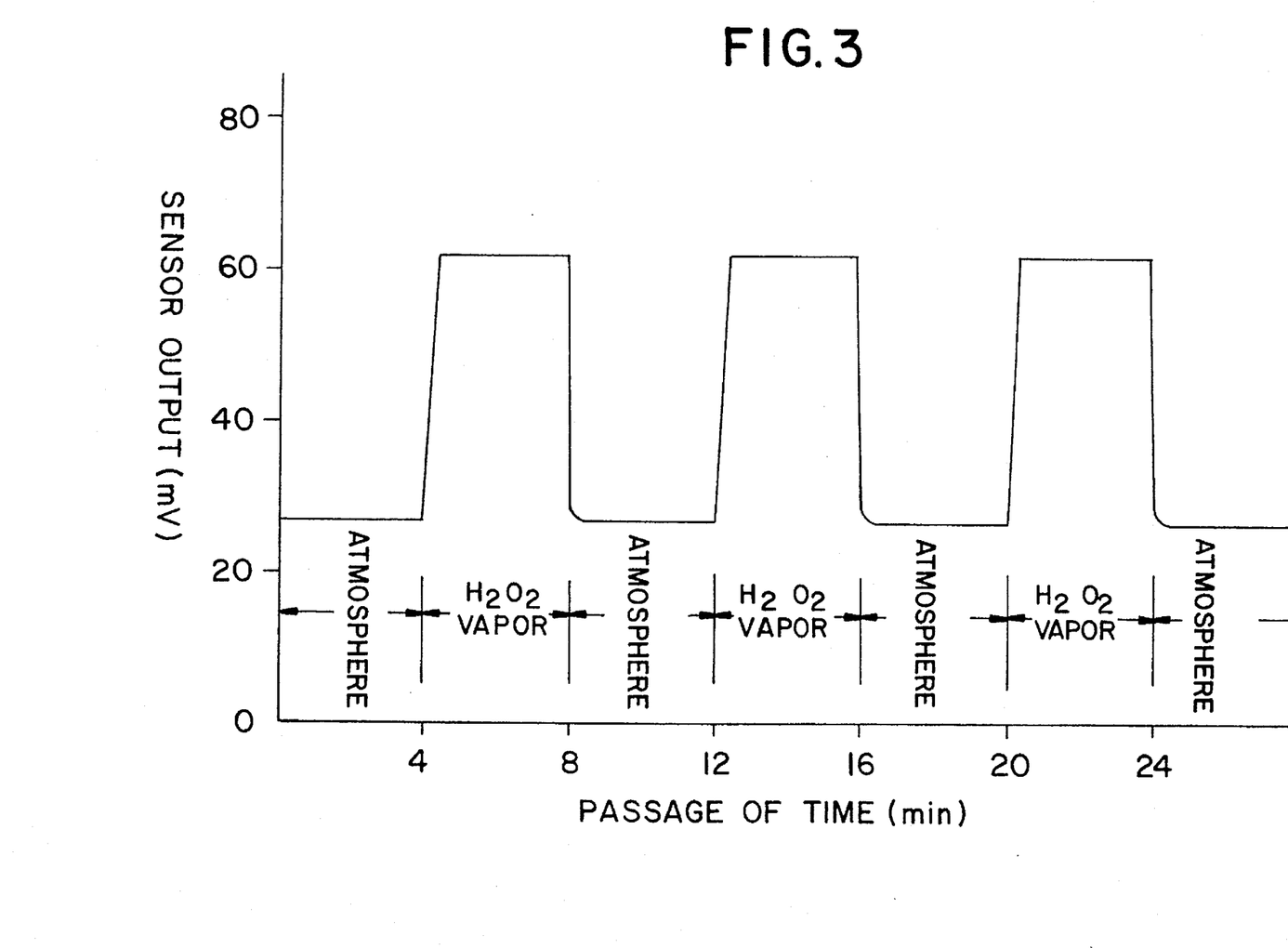
FIG. 3 is a graph showing the response characteristic of the semiconductor gas sensor.
Figure 6:
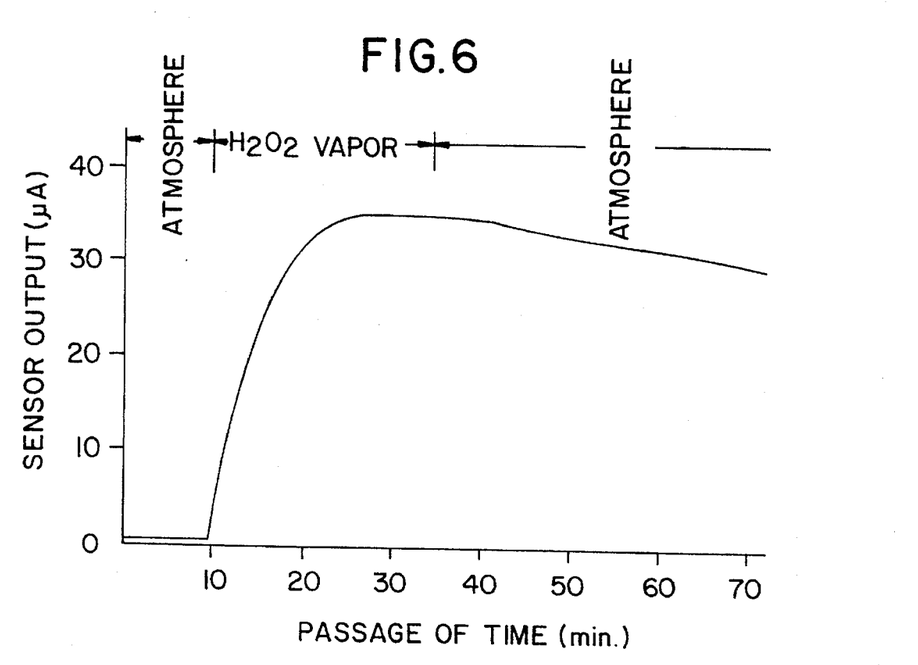
FIG. 6 is a graph showing the response characteristic of the HF sensor.

Incidentally, the clean air (the concentration of the hydrogen peroxide vapor: 0 mg—$H_2O_2$/l) and the hydrogen peroxide vapor having a concentration of 1.4 mg—$H_2O_2$/l was alternately and repeatedly brought into contact with the above-mentioned semiconductor gas sensor 8, and the relation between the lapse of time and the sensor output was obtained. As a result, it was confirmed, as shown in FIG. 3, that the sensor output responds to the concentration of the hydrogen peroxide vapor and the change thereof extremely accurately and quickly. Particularly, in the case where the contact gas was converted from the clean air to the hydrogen peroxide vapor, and in the case where the contact gas was converted from the hydrogen peroxide vapor to the clean air, the response of the semiconductor gas sensor 8 (shown by the time required to output the sensor output corresponding to the concentration of the conversion gas after the point of conversion of the contact gas) was quite fast (within about 30 seconds). Therefore, also from these experiment results, it is easily understood that according to the present invention, the concentration of the hydrogen peroxide vapor 4a and its change in the treatment vessel 2 can be detected accurately on a real-time basis. Incidentally, the similar experiments were conducted in regard to the HF sensor used for the controlled potential electrolysis method described above. But, in this case, as shown in FIG. 6, where the contact gas was converted from clean air (concentration of the hydrogen peroxide vapor: 0 mg—$H_2O_2$/l) to hydrogen peroxide vapor (concentration: 1.4 mg—$H_2O_2$/l), ten plus minutes passed by the time the sensor output corresponding to the concentration of the hydrogen peroxide vapor was output. Thereafter, even if the contact gas was converted from hydrogen peroxide vapor to clean air, the sensor output was hardly changed. Thus, it was confirmed that the response was quite bad as described above, and the concentration of the hydrogen peroxide vapor and its change could not be detected accurately on a real-time basis.

Incidentally, an important thing which is to be noted when implementing the present invention is that the conversion rate from the output by the semiconductor sensor 8 to the value of the concentration of the hydrogen peroxide vapor indicated by the concentration indicator 11 differs according to the conditions of supply of the hydrogen peroxide vapor 4a to the treatment vessel 2 and the conditions of treatment of the subject 1 to be treated by the hydrogen peroxide vapor 4a. Accordingly, as shown in FIG. 2, it is required to know in advance the interrelation between the sensor output and the concentration of the hydrogen peroxide vapor by conducting experiments under the same conditions with the implementation conditions, and to obtain the conversion factor or rate based on this data.

Particularly, when the hydrogen peroxide vapor 4a is supplied to the treatment vessel 2 maintained in an air atmosphere, as in the above-mentioned embodiment, the sensor output and the concentration of the hydrogen peroxide vapor are always in a fixed relationship, and if the concentration of the hydrogen peroxide vapor is the same, the sensor output shows always the same value. But when the hydrogen peroxide vapor 4a is supplied to the treatment vessel 2 maintained in a vacuum atmosphere (less than 760 Torr), the interrelation between the sensor output and the concentration of the hydrogen peroxide vapor is not fixed but changes depending upon the pressure (or the temperature) in the treatment vessel 2. As a result, even if the concentration of the hydrogen peroxide vapor is the same, the sensor output may not show the same value. Accordingly, in such a case the data of interrelation (hereinafter referred to as "correction data") between the sensor output and the concentration of the hydrogen peroxide vapor under the corresponding pressure (or temperature) condition is obtained in advance using the pressure (or the temperature) as the parameter. Based on this correction data, the concentration of the hydrogen peroxide vapor obtained at the sensor output is corrected arithmetically, and indicated by the concentration indicator 11. One example will now be described with reference to FIGS. 4 and 5.

Figure 4:
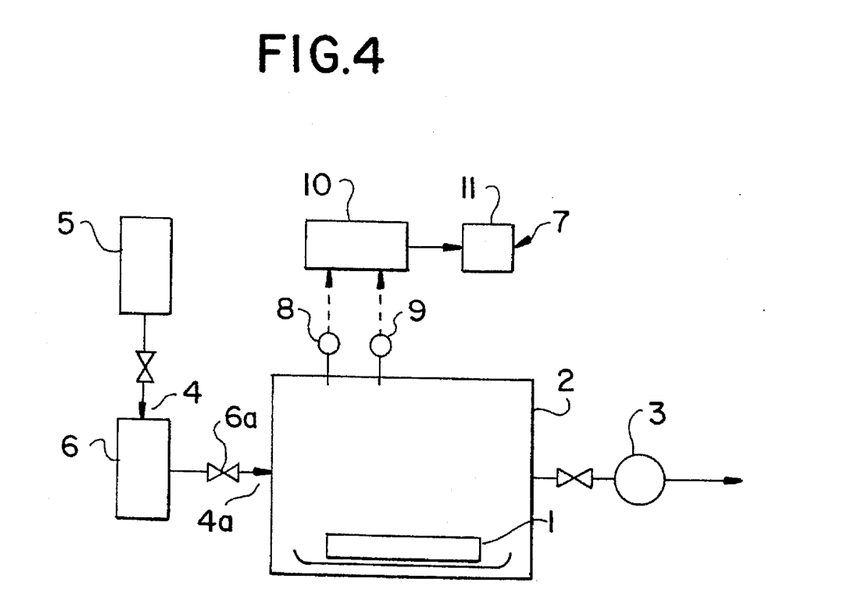
FIG. 4 is a systematic view of the sterilization treatment system showing another embodiment.

Namely, in the sterilization treatment system according to this embodiment, as shown in FIG. 4, after the object 1 to be treated is carried in the treatment vessel 2 and housed therein, the inside of the sealed treatment vessel 2 is vacuum-decompressed by a vacuum pump 3. Then, the hydrogen peroxide vapor 4a is supplied to perform the sterilization treatment of the object 1 to be treated. The sterilization treatment is performed at the standard temperature (25° C. to 30° C.), and the vacuum degree of the treatment vessel 2 is so adjusted that the pressure in the vessel 2 becomes 6 Torr to 30 Torr after the supply of the hydrogen peroxide vapor 4a. Under such condition of supply of the hydrogen peroxide vapor 4a, even if the actual concentration of the hydrogen peroxide vapor (hereinafter referred to as "true concentration") is the same, when the pressure in the treatment vessel 2 changes, the output of the semiconductor sensor 8 changes with the change of the pressure.

The concentration detecting apparatus 7 is, as shown in FIG. 4, includes a semiconductor gas sensor 8, a pressure detector 9 which detects the pressure is the sealed vessel 2, a computing unit 10 to which the detection signal from the semiconductor gas sensor 8 and the pressure detector 9 are always input, and which makes a calculation continuously in comparison with the correction data, and a concentration indicator 11 which indicates the concentration by the input signal from the computing unit 10. The semiconductor sensor 8 is the same as the one used in the above-mentioned embodiment (#812 produced by Figaro Giken Co., Ltd.), and the computing unit 10 stores the correction data obtained from the same sensor as the semiconductor gas sensor 8. The computing unit 10 corrects the detected concentration given by the output of the semiconductor gas sensor 8 in order to make it relevant to the true concentration, by making a calculation in comparison with the correction data obtained under the condition of pressure after gasification corresponding to the relevant pressure, with the pressure detected by the pressure detector 9 being a parameter. The concentration indicator 11 indicates the concentration based on the correction value calculated by the computing unit 10. That is, it does not indicate the detected concentration given by the sensor output as it is, but indicates the concentration corrected by the computing unit 10 as the true concentration.

The correction data sorted in the computing unit 10 is obtained as described below by using the same sensor as the above-mentioned semiconductor gas sensor 8 (#812 produced by Figaro Giken Co., Ltd.).

Namely, the above mentioned sensor is installed in a test vessel in a sealed state (a heat-resistant glass vessel having the capacity of 2.37 l). The inside of the test vessel is maintained in a proper vacuum state by the vacuum pump (hereinafter the pressure in the test vessel in the vacuum state is referred to as "pressure before gasification"). Hydrogen peroxide aqueous solution (having the concentration of 50.14% and the specific gravity of 1.196) is injected into this test vessel by a microsyringe or the like, and is instantaneously heated by a heater or the like so that it may be gasified completely, thereby keeping the pressure in the test vessel (which is the pressure in the test vessel after the hydrogen peroxide aqueous solution has been completely gasified, and hereinafter referred to as "pressure after gasification") at a predetermined level. In the meantime, the sensor output (hereinafter referred to as "data output") is measured. The concentration of the hydrogen peroxide vapor in the test vessel (hereinafter referred to as "data concentration") can be obtained accurately from the capacity of the test vessel, the concentration of the hydrogen peroxide aqueous solution and the quantity thereof to be injected. In addition, the temperature in the test vessel is at a standard temperature (25° C. to 30° C.). And the data output is repeatedly measured under the condition that the pressure after gasification is the same while changing the quantity of the hydrogen peroxide aqueous solution as injected into the test vessel to obtain the interrelation between the data output and the data concentration at the corresponding pressure after gasification. This interrelation is obtained with respect to each pressure after gasification, while changing the pressure after gasification in a range relevant to the range (6 Torr to 30 Torr) of the pressure change in the treatment vessels 2 at the sterilization treatment. For example, after the pressure before gasification is adjusted by a vacuum pump in the range of 1 Torr to 25 Torr so that the pressure after gasification stands at 6 Torr, 10 Torr, 20 Torr and 30 Torr, the interrelation between the data output and the data concentration at each pressure after gasification is obtained.

Figure 5:
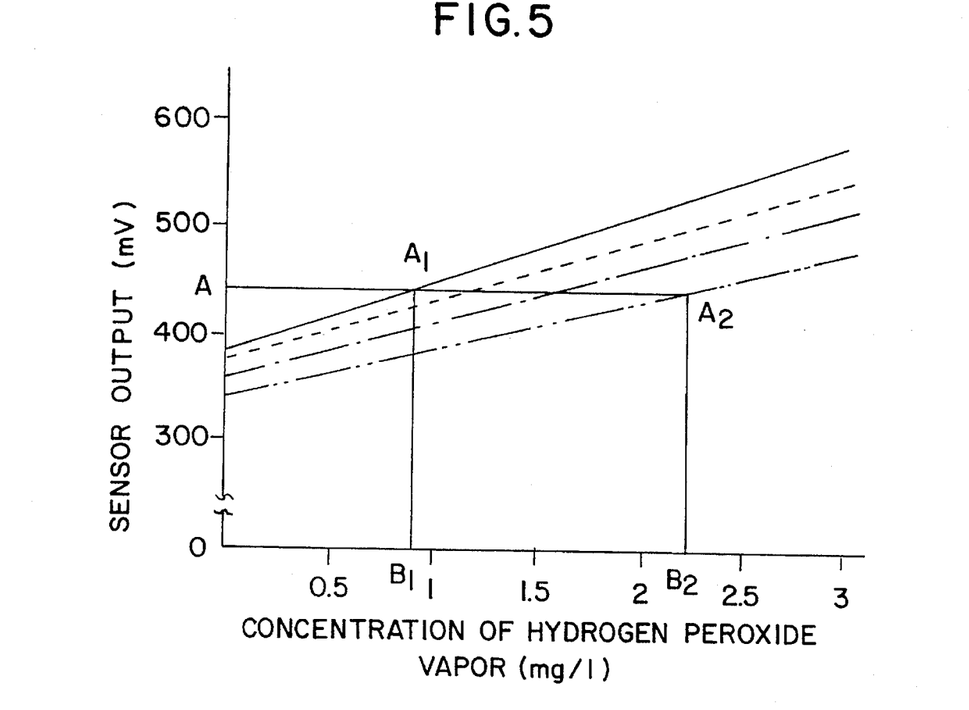
FIG. 5 is a graph showing the interrelation between the output of the semiconductor gas sensor and the concentration of the hydrogen peroxide vapor using the pressure as a parameter.

Thus, the correction data as shown in FIG. 5 is obtained. In FIG. 5, for convenience sake, only the cases where the pressures after gasification are 6 Torr (solid line), 10 Torr (broken line), 20 Torr (one-dot chain line) and 30 Torr (two-dot chain line) are shown.

In addition to the sensor output, the pressure in the sealed vessel 2 is input by the pressure detector 9 to the computing unit 10 which stores these correction data, and the correction data corresponding to the relevant pressure is selected. The sensor output is corrected by calculation in comparison with the correction data selected with the pressure being a parameter, and the value equivalent to the data concentration which corresponds to the data output equivalent to said sensor output is indicated by the concentration indicator 11 as the detected concentration. Concretely, for example, in the case where the sensor output is A, as shown in FIG. 5, when the detected pressure by the pressure detector 9 is 6 Torr, the correction data shown in a solid line is selected. By calculation in comparison with this correction data, the data concentration $B_1$ corresponding to the data output $A_1$ which is equivalent to the sensor output A is extracted, and the value equivalent to this data concentration $B_1$ is indicated by the concentration indicator 11 as the detected concentration. Moreover, even if the sensor output is the same A, the correction data shown in the two-dot chain line is selected when the detected pressure is 30 Torr. By calculation in comparison with this correction data, the data concentration $B_2$ corresponding to the data output $A_2$ equivalent to the sensor output A is extracted, and the value equivalent to this data concentration $B_2$ is indicated by the concentration indicator 11 as the detected concentration.

Thus, even if the sensor output is the same, the data output equivalent to the sensor output in the correction data obtained under the condition of the pressure after gasification equivalent to the relevant pressure is extracted with the pressure in the scaled vessel 2 being a parameter, and the detected concentration given by the semiconductor gas sensor 8 is corrected to the value equivalent to the data concentration corresponding to said data output. Therefore, since the correction data shows the interrelation between the sensor output and the true concentration under the state that the pressure after gasification is maintained at a constant level, the detected concentration which has been corrected shows the true concentration, and the concentration detection (or the concentration indication by the concentration indicator 11) can be performed accurately.

In addition, the present invention is not limited to each embodiment described above, and can be changed or modified properly without departing from the spirit and the scope of the present invention. For example, by controlling automatically the supply nozzle 6a (or the gasifying device 6 or the like) by the signal which is output from the semiconductor sensor 8 in the embodiment shown in FIG. 1, or by the signal which is output from the computing unit 10 in the embodiment shown in FIG. 4, it is possible to control automatically the concentration in the treatment vessel 2. Furthermore, as shown in FIG. 4, in the case where the hydrogen peroxide vapor 4a is supplied to the treatment vessel 2 maintained in a vacuum atmosphere, it is preferred that if the temperature in the treatment vessel 2 is not standard, the correction of the detected concentration given by the sensor output be performed with the temperature as well as the pressure being the parameters. This is because under the condition that the temperature is not standard, there is a threat that the sensor output may be changed depending on the temperature. It is a matter of course, in such as case, that the interrelation between the sensor output and the concentration need be obtained with the temperature also being the independent parameter. The method to obtain this data and the method to calculate the data are similar to the methods by which the correction data described above was obtained. Furthermore, the present invention is not particularly limited to the case where it is applied to the above-mentioned sterilization treatment system, but can be applied to all kinds of systems and instruments which perform any treatment by supplying the hydrogen peroxide vapor to a closed vessel.

As is apparent from the description given above, according to the method for detecting the concentration of the present invention, the concentration of the hydrogen peroxide vapor and the change thereof in the treatment vessel can be detected or monitored directly and accurately on a real-time basis, and the sterilization treatment and the like by the hydrogen peroxide vapor can be performed efficiently and adequately. Furthermore, according to the apparatus for detecting the concentration of the present invention, said method can be implemented without any accompanying problems.

We claim:

1. A method for detecting a concentration of hydrogen peroxide vapor in a treatment vessel for sterilization treatment of an object with hydrogen peroxide vapor, comprising the steps of:

arranging a semiconductor gas sensor sensitive to hydrogen peroxide inside the treatment vessel with an output proportional to the hydrogen peroxide vapor concentration therein;

arranging a concentration indicator outside the treatment vessel;

supplying hydrogen peroxide vapor to said vessel in a flow regulated amount that is controlled according to the concentration measured by said sensor;

indicating the concentration of hydrogen peroxide vapor with said indicator using an output of said sensor.

2. A method for detecting a concentration of hydrogen peroxide vapor according to claim 1, wherein when the hydrogen peroxide vapor is supplied to said treatment vessel, and the vessel is maintained in an air atmosphere not containing any hydrogen peroxide vapors, a value obtained by converting the output of said semiconductor gas sensor with a fixed conversion factor is indicated by said concentration indicator as the concentration of the hydrogen peroxide vapor in the treatment vessel.

3. A method for detecting a concentration of hydrogen peroxide vapor according to claim 1, wherein when the hydrogen peroxide vapor is supplied to said treatment vessel, and the vessel is maintained in a vacuum, the output of said semiconductor gas sensor is arithmetically corrected, based on the pressure in said treatment vessel, using data, obtained in advance, representing the relationship between the sensor output and the concentration of the hydrogen peroxide vapor under a given pressure.

4. An apparatus, comprising:

a treatment vessel for treating an object with hydrogen peroxide, a semiconductor gas sensor sensitive to hydrogen peroxide arranged inside the treatment vessel and having an output proportional to the hydrogen peroxide vapor concentration therein, and a source of hydrogen peroxide and means for supplying hydrogen peroxide to the vessel in a flow regulated amount that is controlled according to the concentration measured by said sensor, a concentration indicator arranged outside the treatment vessel for converting the output of the semiconductor gas sensor to an indicated value of hydrogen peroxide concentration.

5. An apparatus according to claim 4, adapted to be used when the hydrogen peroxide vapor is supplied to said treatment vessel, and the vessel is maintained in an air atmosphere, wherein said concentration indicator indicates a concentration of hydrogen peroxide vapor in said treatment vessel converted from the output of said semiconductor gas sensor by a fixed conversion factor.

6. An apparatus according to claim 4, adapted to be used when the hydrogen peroxide vapor is supplied to said treatment vessel when the vessel is maintained in a vacuum, comprising a pressure detector for detecting the pressure in said treatment vessel, and a computing unit which arithmetically corrects the sensor output, based on the pressure in the closed vessel, using data, obtained in advance, representing the relationship between the sensor output and the concentration of the hydrogen peroxide vapor in the vessel under a given pressure, said concentration indicator being modified to receive this adjusted output and to indicate the correction value obtained by said computing unit and provide a true corrected output of the concentration of the hydrogen peroxide vapor in said treatment vessel.

* * * * *